(12) United States Patent
Hossainy et al.

(10) Patent No.: US 8,911,766 B2
(45) Date of Patent: Dec. 16, 2014

(54) DRUG DELIVERY COMPOSITIONS INCLUDING NANOSHELLS FOR TRIGGERED DRUG RELEASE

(75) Inventors: Syed F. A. Hossainy, Fremont, CA (US); John J. Stankus, Campbell, CA (US); Dariush Davalian, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1014 days.

(21) Appl. No.: 12/493,112

(22) Filed: Jun. 26, 2009

(65) Prior Publication Data

US 2010/0330147 A1  Dec. 30, 2010

(51) Int. Cl.

| A61K 9/14 | (2006.01) |
|---|---|
| A61K 9/00 | (2006.01) |
| A61K 9/51 | (2006.01) |
| A61K 9/16 | (2006.01) |
| A61K 9/50 | (2006.01) |
| A61L 29/16 | (2006.01) |
| A61L 31/16 | (2006.01) |
| A61L 27/54 | (2006.01) |
| A61M 25/10 | (2013.01) |
| A61M 25/00 | (2006.01) |

(52) U.S. Cl.
CPC ........ *A61K 9/0009* (2013.01); *A61M 2025/105* (2013.01); *A61K 9/5153* (2013.01); *A61K 9/1641* (2013.01); *A61K 9/5031* (2013.01); *A61L 29/16* (2013.01); *A61L 31/16* (2013.01); *Y10S 977/906* (2013.01); *A61L 27/54* (2013.01); *A61L 2300/602* (2013.01); *A61K 9/5146* (2013.01); *A61L 2300/45* (2013.01); *A61M 2025/0057* (2013.01); *A61L 2400/12* (2013.01); *A61M 25/0045* (2013.01); *A61K 9/1647* (2013.01); *Y10S 977/773* (2013.01)
USPC .......... 424/426; 424/489; 977/773; 977/906; 977/773

(58) Field of Classification Search
None
See application file for complete search history.

(56) References Cited

U.S. PATENT DOCUMENTS

| 4,293,539 | A | 10/1981 | Ludwig et al. |
|---|---|---|---|
| 4,622,244 | A | 11/1986 | Lapka et al. |
| 4,897,268 | A | 1/1990 | Tice et al. |
| 4,954,298 | A | 9/1990 | Yamamoto et al. |
| 6,224,794 | B1 | 5/2001 | Amsden et al. |
| 6,528,093 | B1 | 3/2003 | Camei et al. |
| 6,645,517 | B2 | 11/2003 | West et al. |
| 6,660,381 | B2 | 12/2003 | Halas et al. |
| 6,685,986 | B2 | 2/2004 | Oldenburg et al. |
| 6,692,466 | B1 | 2/2004 | Chow et al. |
| 6,699,724 | B1 | 3/2004 | West et al. |
| 6,767,637 | B2 | 7/2004 | Park et al. |
| 7,048,947 | B2 | 5/2006 | Camei et al. |
| 7,060,299 | B2 | 6/2006 | Alavattam et al. |
| 8,034,361 | B2 | 10/2011 | Hossainy et al. |
| 8,048,441 | B2 | 11/2011 | Craig et al. |
| 2002/0061363 | A1 | 5/2002 | Halas et al. |
| 2002/0132045 | A1 | 9/2002 | Halas et al. |
| 2002/0164064 | A1 | 11/2002 | Karklin et al. |
| 2002/0187347 | A1 | 12/2002 | Halas et al. |
| 2004/0052858 | A1 | 3/2004 | Wu et al. |
| 2004/0052859 | A1 | 3/2004 | Wu et al. |
| 2005/0056118 | A1 | 3/2005 | Xia et al. |
| 2007/0055364 | A1 | 3/2007 | Hossainy et al. |
| 2007/0148251 | A1 | 6/2007 | Hossainy et al. |
| 2007/0185150 | A1* | 8/2007 | Bedrosian ..................... 514/299 |
| 2007/0258903 | A1 | 11/2007 | Kleiner et al. |
| 2007/0292495 | A1* | 12/2007 | Ludwig et al. ................ 424/450 |
| 2007/0292518 | A1 | 12/2007 | Ludwig |
| 2007/0298257 | A1 | 12/2007 | Ludwig et al. |
| 2008/0146489 | A1 | 6/2008 | Pacetti et al. |
| 2009/0005861 | A1 | 1/2009 | Hossainy et al. |
| 2009/0148491 | A1 | 6/2009 | Hossainy et al. |
| 2009/0324670 | A1 | 12/2009 | Wang |
| 2010/0104506 | A1 | 4/2010 | Ludwig et al. |
| 2011/0184384 | A1 | 7/2011 | Davalian et al. |
| 2011/0196187 | A1 | 8/2011 | Ludwig et al. |
| 2011/0196474 | A1 | 8/2011 | Davalian et al. |

FOREIGN PATENT DOCUMENTS

WO    WO 01/05586    1/2001

OTHER PUBLICATIONS

R Auras, B Harte, S Selke. "An Overview of Polylactides as Packaging Materials." Macromolecular Biosciences, vol. 4, 2004, pp. 835-864.*

A Sodergard, M Stolt. "Properties of Lactic Acid Based Polymers and Their Correlation with Composition." Progress in Polymer Science, vol. 27, 2002, pp. 1123-1163.*

M Hamoudeh, A Al Faraj, E Canet-Soulas, F Bessueille, De Leonard, H Fessi. "Elaboration of PLLA-based superparamagnetic nanoparticles: Characterization, magnetic behaviour study and in vitro relaxivity evaluation." International Journal of Pharmaceutics, vol. 338, 2007, pp. 248-257.*

OC Farokhzad, S Jon, A Khademhosseini, TNT Tran, Da LaVan, R Langer. "Nanoparticle-Aptamer Bioconjugates: A New Approach for Targeting Prostate Cancer Cells." Cancer Research, vol. 64, Nov. 1, 2004, pp. 7668-7672.*

(Continued)

*Primary Examiner* — Frederick Krass
*Assistant Examiner* — Isaac Shomer
(74) *Attorney, Agent, or Firm* — Squire Patton Boggs (US) LLP (57) ABSTRACT

The current invention is directed to compositions comprising a plurality of particles including nanoshells or a medical device with a coating including nanoshells allowing for triggered drug release. Methods of treatment with such compositions are also included.

23 Claims, 4 Drawing Sheets

(56) References Cited

OTHER PUBLICATIONS

AR Lowery. "Nanoshell-Assisted Cancer Therapy: Targeted Photothermal Tumor Ablation." Rice University PhD Thesis, Apr. 2007. Pages include first two pages (not numbered), pp. i-xiii and 1-122.*
Berkland et al., "Fabrication of PLG microspheres with precisely controlled and monodisperse size distributions", J. of Controlled Release 73, pp. 59-74 (2001).
Berkland et al., "Precision Polymer Microparticles for Controlled-Release Drug Delivery", Am Chem. Soc. pp. 197-213 (2004).
Oldenburg et al., "Infrared extinction properties of gold nanoshells", Applied Phys. Letters 75, No. 19, pp. 2897-2899 (1999).
Oldenburg et al., "Nanoengineering of optical resonances", Chem. Phys. Letters 288, pp. 243-247 (1998).
Polyethylene Glycol, product information, downloaded from: www.jtbaker.com/msds/englishhtml, 4 pgs., May 28, 2009.
U.S. Appl. No. 11/636,092, filed Dec. 8, 2006, Hossainy et al.
U.S. Appl. No. 11/945,977, filed Nov. 27, 2007, Ludwig et al.
Discher et al., "Polymersomes:Tough Vesicles Made from Diblock Copolymers", Science vol. 284, No. 5417, pp. 1143-1146 (1999) Abstract 1 pg.

* cited by examiner

DRUG DELIVERY COMPOSITIONS INCLUDING NANOSHELLS FOR TRIGGERED DRUG RELEASE

FIELD

This invention relates to organic chemistry, polymer chemistry, physiology, material science, drug delivery, medical devices, and diagnostic devices that are coupled to a mechanism of activating drug delivery.

BACKGROUND

Modulated drug delivery refers to matching the release profiles of drugs to the physiological requirements of the patient. This type of controlled delivery is useful for treating diseases that affect the homeostatic functions of the body, such as diabetes mellitus. Insulin therapy for diabetes requires a low baseline release of the drug, with peaks after the ingestion of food.

Various methods of accomplishing modulated in vivo drug delivery have been described in the literature. Mechanical pumps are one type of device that is commonly employed. Another method that has been examined is the use of ultrasound to rupture microcapsules or strip a layer of material from a drug-containing polymer matrix to alter drug release. Potential problems with such ultrasound techniques include concurrent rupture of cells at high levels of insonation power and concern about the long term safety of repetitive exposure of body tissues to ultrasonic energy.

Certain temperature sensitive hydrophilic polymer gels (hydrogels) have been described as another means of modulating drug delivery. When the temperature of the polymer is raised above its lower critical solution temperature (LCST), the hydrogel undergoes a reversible phase transition that results in the collapse of the hydrogel structure. The hydrogel collapse forces soluble materials held within the hydrogel matrix to be expelled into the surrounding solution. An impediment to the development of temperature-sensitive materials into clinically useful modulated drug delivery devices has been the lack of satisfactory means for altering the temperature of the implanted device.

Safe and efficient alternative compositions and methods for triggered drug release are provided herein. In addition, on-demand, adaptive drug delivery systems and methods are provided, including triggered drug release.

SUMMARY

An aspect of the present invention is a composition for controlled release of a drug comprising:
  a plurality of particles comprising:
    an amorphous or semi-crystalline polymer with a glass transition temperature as plasticized under physiological conditions from about 40° C. to about 60° C., or a semi-crystalline polymer having a degree of crystallinity of at least 25% with a melting temperature, as plasticized under physiological conditions, from about 40° C. to about 60° C.;
    a drug; and
    one or more nanoshells capable of producing heat upon exposure to electromagnetic radiation, a fluctuating magnetic field, or a microwave field;
  wherein substantially all of the individual particles of the plurality include one or more of the nanoshells.

In an aspect of this invention, the average diameter of the particles is about 50 nanometers to about 10 micrometers.

In an aspect of this invention, the polymer comprises a coating on the particles.

In an aspect of this invention, the particles are composed entirely of a polymer matrix.

Another aspect of this invention is an implantable medical device, comprising:
  a device body having an outer surface;
  an optional primer layer disposed over the outer surface; and
  a coating comprising:
    an amorphous or semi-crystalline polymer with a glass transition temperature as plasticized under physiological conditions from about 40° C. to about 60° C., or a semicrystalline polymer having a degree of crystallinity of at least 25% with a melting temperature, as plasticized under physiological conditions, from about 40° C. to about 60° C.;
    a drug; and
    a plurality of nanoshells capable of producing heat upon exposure to electromagnetic radiation, a fluctuating magnetic field, or a microwave field;
  wherein the coating comprises one or more layers disposed over the outer surface or over the primer layer, if opted for.

In an aspect of this invention, the coating comprises a first coating layer disposed over the outer surface or the primer layer if opted for, the first coating layer comprising a drug; and a second coating layer, disposed over the first coating layer, comprising the polymer and the nanoshells.

In an aspect of this invention, upon exposure to electromagnetic radiation, a fluctuating magnetic field, or a microwave field the nanoshells produce sufficient heat to raise the temperature of the polymer above its glass transition temperature or its melting temperature.

In an aspect of this invention, the glass transition temperature or the melting temperature of the polymer is from about 40° C. to about 50° C.

In an aspect of this invention, the nanoshells comprise gold.

In an aspect of this invention, the average diameter of the nanoshells is about 15 nanometers to about 200 nanometers.

In an aspect of this invention, the nanoshells comprise cores comprising iron, iron oxide, lanthanides, samarium, gadolinium, europium, terbium, tantalum, molybdenum, alloys thereof, and combinations thereof.

In an aspect of this invention, the nanoshells comprise silver, platinum, palladium, chromium, iridium, magnesium, zinc, calcium, tungsten, or alloys or combinations thereof.

In an aspect of this invention, the polymer is selected from the group consisting of poly(L-lactide-co-glycolide), poly(D,L-lactide), poly(L-lactide), polyglycolide, poly(D,L-lactide-co-glycolide), poly(glycolide), polycaprolactone, poly(lactide-co-caprolactone), poly(glycolide-co-caprolactone), biodegradable polyurethanes, poly(hydroxybutyrate), poly(hydroxyvalerate), poly(ethylene glycol), poly(ethylene glycol)-poly(L-lactide) diblock copolymers, poly(ethylene glycol)-poly(L-lactide-glycolide) diblock copolymers, poly(L-lactide-glycolide)-poly(ethylene glycol)-poly(L-lactide-glycolide) triblock copolymers, poly(hydroxybutyrate-co-valerate), block copolymers of poly(ethylene oxide) and poly(propylene oxide), polyphosphoester urethane, poly(amino acids), poly(trimethylene carbonate), poly(ether-esters), polyphosphazenes, and combinations thereof.

In an aspect of this invention, the drug is selected from the group consisting of actinomycins, taxol paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl(4-amino-TEMPO), biolimus A9, deforolimus, AP23572, temsirolimus, pimecrolimus, 40-O-tetrazolyl-rapamycin, 40-epi-(N1-tetrazole)-rapamycin, pirfenidone, tacrolimus, dexamethasone, rapamycin, 40-O-(2-hydroxy)ethyl-rapamycin(everolimus), 40-O-(3-hydroxy)propyl-rapamycin, 40-O-[2-(2-hydroxy)ethoxy] ethyl-rapamycin, and 40-O-tetrazole-rapamycin, zotarolimus, γ-hiridun, clobetasol, pimecrolimus, imatinib mesylate, or midostaurin, or any combinations thereof.

In an aspect of this invention, the composition comprises at least two drugs, the two drugs comprising a statin and an anti-inflammatory drug, or a statin and fenofibrate, and in a further aspect of this invention, the composition is capable of releasing both drugs at respective optimal release rates modulated when the composition is exposed to electromagnetic radiation, a fluctuating magnetic field, or a microwave field.

Another aspect of this invention is a method comprising: administering to a patient in need thereof the plurality of particles; and applying a fluctuating magnetic field, a microwave field, or an electromagnetic radiation to the composition.

In an aspect of this invention, administering the plurality of particles comprises systemic or local administration.

In an aspect of this invention, systemic administration comprises intravenous injection, intramuscular injection, or injection into the bone marrow.

In an aspect of this invention, local administration comprises administration by a catheter, a coated balloon catheter, a needle-injection catheter, a porous balloon catheter, local needle injection, implantation of a coated stent, implantation of a biodegradable stent, implantation of a biodegradable implant, or any combination thereof.

Another aspect of this invention is a method comprising implanting into a patient in need thereof an implantable medical device as described above, and applying to the device a fluctuating magnetic field, a microwave field, or an electromagnetic radiation.

In an aspect of this invention, the fluctuating magnetic field, the microwave field, or the electromagnetic radiation is applied outside the patient's body.

In an aspect of this invention, the fluctuating magnetic field, the microwave field, or the electromagnetic radiation is applied inside the patient's body.

In an aspect of this invention, application within a patient's body comprises using a catheter.

In an aspect of this invention, the patient is in need of treatment for a disease or condition selected from the group consisting of atherosclerosis, vulnerable plaque, restenosis, peripheral vascular disease, small vessel bifurcations and cancer.

DETAILED DESCRIPTION

DISCUSSION

Use of the singular herein includes the plural and vice versa unless expressly stated to be otherwise. That is, "a" and "the" refer to one or more of whatever the word modifies. For example, "a drug" may refer to one drug, two drugs, etc. Likewise, "the polymer" may mean one polymer or a plurality of polymers. By the same token, words such as, without limitation, "drugs" and "polymers" refer to one drug or polymer as well as to a plurality of drugs or polymers unless it is expressly stated or obvious from the context that such is not intended.

As used herein, unless specified otherwise, any words of approximation such as without limitation, "about," "approximately," "essentially," "substantially" and the like mean that the element so modified need not be exactly what is described but can vary from the description by as much as ±15% without exceeding the scope of this invention.

As used herein, any ranges presented are inclusive of the end-points. For example, "a temperature between 10° C. and 30° C." or "a temperature from 10° C. to 30° C." includes 10° C. and 30° C., as well as any temperature in between.

As used herein, the use of "preferred," "preferably," "more preferred," and the like to modify an aspect of the invention refers to preferences as they existed at the time of filing of the patent application.

As used herein, a "polymer" is a molecule made up of the repetition of a simpler unit, herein referred to as a constitutional unit. The constitutional units themselves can be the product of the reactions of other compounds. A polymer may comprise one or more types of constitutional units. As used herein, the term polymer refers to a molecule comprising 2 or more constitutional units. Polymers may be straight or branched chain, star-like or dendritic, or one polymer may be attached (grafted) onto another. Polymers may have a random disposition of constitutional units along the chain, the constitutional units may be present as discrete blocks or segments, or constitutional units may be so disposed as to form gradients of concentration along the polymer chain. Polymers may be cross-linked to form a network.

As used herein, "copolymer" refers to a polymer which includes more than one type of constitutional unit.

As used herein, a "polymer segment" refers to a polymeric species that comprises a part of a larger polymer. For example for a block copolymer of constitutional units x, y, and z, a string of x constitutional units may constitute a segment. The segment itself may also be considered a polymer although it is part of a larger molecule. The segment may be made up of more than one type of constitutional unit. Thus they are referred to herein as "polymer segments" or sometime simply "segments." The terms are used interchangeably herein.

As used herein, "biocompatible" refers to a polymer or other material that both in its intact, that is, as synthesized, state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

As used herein, the terms "biodegradable", "bioerodable", "bioabsorbable," "degraded," "eroded," "absorbed," and "dissolved," are used interchangeably, and refer to a substance that is capable of being completely or substantially completely, degraded, dissolved, and/or eroded over time when exposed to physiological conditions (pH, temperature, enzymes and the like), and can be gradually eliminated by the body, or that can be degraded into fragments that can pass through the kidneys. Conversely, "biostable" refers to a substance that is not biodegradable, etc.

The glass transition temperatures, $T_g$, is the temperature at which an amorphous polymer or amorphous segment of a polymer changes mechanical properties from those of a rubber (i.e., elastic) to those of a glass (brittle). The $T_g$ of a given polymer/polymer segment depends on its thermal history as well as the method used to measure it. For the purposes of this invention, any reference to a $T_g$ is understood to be that obtained by differential scanning calorimetry (DSC). The chemical structure of the polymer heavily influences $T_g$ by affecting chain mobility. Below the $T_g$ the polymeric molecules have very little rotational or translational freedom, i.e., they are unable to rotate or move easily or very far in relation to one another. Above $T_g$, relatively facile segmental motion becomes possible and the polymer chains are able to move around and slip by one another.

Plasticization of a polymer refers to lowering the $T_g$ of the polymer by adding a lower molecular weight material to a polymer. Exemplary plasticizers include, without limitation, phthalate, trimellitate, sebacate and maleate esters, epoxidized vegetable oils, sulfonamides, organophosphates, glycols and polyethers.

As used herein, a material that is described as a layer, a film, a coating, or a coating layer "disposed over" a substrate refers to deposition of the material directly or indirectly over at least a portion of the surface of that substrate. "Directly deposited" means that the material is applied directly to the surface of the substrate. "Indirectly deposited" means that the material is applied to an intervening layer that has been deposited directly or indirectly over the substrate. The terms "layer," "film," "coating" and "coating layer" are used interchangeably herein. Unless the context clearly indicates otherwise, a reference to a layer, film, coating, or coating layer refers to such covering all, or substantially all, of the surface over which it is disposed, directly or indirectly.

As used herein, a "coating formulation" refers to the mixture of substances disposed over a substrate. If substances are dissolved or dispersed in a solvent to form a "coating solution," and the coating solution is disposed over a substrate followed by removal of the solvent, the solvent is not part of the "coating formulation." However, the layer deposited may contain small amounts of residual solvent.

As used herein, a "primer layer" refers to a coating consisting of a material such as, without limitation, a polymer, that exhibits good adhesion to the material of which the substrate is manufactured, and also good adhesion to whatever material is to be coated on the substrate. Thus, a primer layer serves as an adhesive intermediary layer between a substrate and materials to be carried by the substrate and is, therefore, applied directly to the substrate. Preferred substrates are medical device bodies, and nanoshells. Non-limiting examples of primers for use with device bodies, and potentially for use with nanoshells, include silanes, titanates, zirconates, silicates, parylene, polyacrylates and polymethacrylates.

As used herein, a "drug" refers to any substance that, when administered in a therapeutically effective amount to a patient suffering from a disease or condition, has a therapeutic beneficial effect on the health and well-being of the patient. A therapeutic beneficial effect on the health and well-being of a patient includes, but it not limited to: (1) curing the disease or condition; (2) slowing the progress of the disease or condition; (3) causing the disease or condition to retrogress; or, (4) alleviating one or more symptoms of the disease or condition.

As used herein, a drug also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "drug" also refers to pharmaceutically acceptable, pharmacologically active derivatives of those drugs specifically mentioned herein, including, but not limited to, salts, esters, amides, and the like. Substances useful as diagnostics are also encompassed by the term "drug."

As used herein, an "organic solvent" is a fluid the chemical composition of which includes carbon atom(s). The fluid may be liquid, gaseous or in a supercritical state. An organic solvent herein may be a blend of two or more such fluids.

As used herein, a "particle" simply refers to a macroscopic fragment of material of no particular shape composed of an agglomeration of individual molecules of one or more compounds. For the purposes of this disclosure, a particle can range in size from less than a one tenth of a nanometer to several millimeters.

As used herein, the "average diameter" of a plurality of particles refers to diameters determined by dynamic light scattering (DLS), also referred to as photo correlation spectroscopy. Dynamic light scattering determines the hydrodynamic diameter (Stokes diameter) based on diffusion measurements, and includes solvent associated with the particle. For non-spherical particles, the reported "diameter" is actually the effective diameter of a sphere with the equivalent hydrodynamic radius. This mean hydrodynamic diameter obtained from DLS is close to the volume-average diameter. A non-limiting example of a method for determining average diameters is International Standards Organization (ISO) 13321.

There are a number of other ways of representing the average diameter of a group of particles. The average diameter can be a number average diameter, where the number average diameter=$\Sigma_i d_i n_i / \Sigma_i n_i$ where $n_i$ represents the number of particles with a diameter represented by $d_i$. The surface area average diameter is determined by $(\Sigma_i f_i d_i^2)^{1/2}$, and the volume average diameter is determined by $(\Sigma_i f_i d_i^3)^{1/3}$, where $f_i$ is $n_i/\Sigma_i n_i$. The volume average is greater than the surface area average diameter, which is greater than the number average diameter. The mass or weight average diameter is the same as the volume average diameter if the density of all of the particles is the same. For the purposes of this invention, any manner of average diameter determination can be used so long as the result is correlated with that obtained by DLS, the technique used herein.

Particles are generally polydisperse, i.e., not all the same size. One measure of polydispersity is the ratio D90/D10. D90 and D10 are the diameters below which 90% and 10% of the particles fall for a number average diameter, or 90% or 10% of the surface area of the particles fall for a surface area average diameter, and the like. As used herein, unless specified otherwise, the D90 and D10 are the diameters taken from the cumulative particle size distribution as determined by DLS.

As used herein, "nano-particles" refer to particles with an average diameter from 1 nm to 10 μm.

As used herein, "micro-particles" refer to particles with an average diameter from 10 μm to about 1000 μm.

As used herein, "burst release" refers to the release of a drug from a drug delivery system within a very short time, or a large increase in drug release within a very short time.

As used herein, "release rate" refers to the amount of drug released from a drug delivery system per unit of time, for example without limitation 0.1 mg per hour (0.1 mg/hr) or 100 mg per day.

As used herein, "release duration," refers to the total time over which a drug is released in a therapeutically effective amount from a drug delivery system. For example without limitation, a drug release duration of 1 hour, 72 hours or 6 months means that a therapeutically effective amount of the drug is released over that time period.

As used herein, any measurement of drug release, for example without limitation, release rate or release duration, refers to the an in vitro measurement using a United States Pharmacopeia Type VII apparatus and porcine serum at a temperature of 37° C., with sodium azide optionally added (for example at 0.1% w/v).

A polymer matrix refers to a three dimensional construct in which one or more polymers forms a continuous phase. A polymer matrix may include other materials, non-limiting examples of which are drugs and plasticizers. Other materials may be dispersed within the matrix, homogeneously or substantially homogeneously, to form a separate phase.

The "percolation threshold" is the point at which domains of a discrete phase in a multiple phase system begin to connect and form an interconnected network within the continuous phase. Percolation thresholds are generally expressed as a volume fraction and are a function of the domain size and shape for each of the phases in the multiple phase system.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; may be until the device biodegrades; or may be until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves, foramen ovale closure devices, cerebrospinal fluid shunts, and intrauterine devices. An implantable medical device specifically designed and intended solely for the localized delivery of a drug is within the scope of this invention. Implantable medical devices can be made of virtually any material including metals and/or polymers.

One form of implantable medical device is a "stent." A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease such as, without limitation, atherosclerosis, carotid artery disease, peripheral arterial disease (PAD), restenosis and vulnerable plaque. For treatment of PAD, stents may be used in peripheral arties such as the superficial femoral artery (SFA).

As used herein a "device body" refers to an implantable medical device in a fully formed utilitarian state with an outer surface to which no coating or layer of material different from that of which the device itself is manufactured has been applied. By "outer surface" is meant any surface however spatially oriented that is in contact with bodily tissue or fluids. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what it is made of.

As used herein, a "catheter" is a thin, flexible tube for insertion into the body. Catheters may be used to remove or introduce fluid. One form of catheter is a vascular catheter. A vascular catheter is a thin, flexible tube with a manipulating means at one end, referred to as the proximal end, which remains outside the patient's body, and an operative device at or near the other end, called the distal end, which is inserted into the patient's artery or vein. A vascular catheter may have a balloon disposed on the distal end, and/or may be used to delivery a stent to an artery. Another form of catheter is a urinary catheter.

As used herein, a "balloon" refers to the well-known in the art device, usually associated with a vascular catheter, that comprises a relatively thin, elastomeric material that when positioned at a particular location in a patient's vessel can be expanded or inflated to an outside diameter that is essentially the same as the inside or luminal diameter of the vessel in which it is placed.

The present invention is directed to drug delivery compositions allowing for triggered drug release, and methods of using such compositions. The drug delivery compositions comprise a polymer, a drug, and nanoshells. The polymer, drug and nanoshells may be included in a coating and/or in particles. The nanoshells are capable of heating up as a result of absorption of electromagnetic radiation, or exposure to a fluctuating magnetic field. Due to heating of the nanoshells, the polymer is heated to a temperature above its glass transition temperature or its melt temperature resulting in a change in the diffusivity of the drug, and thus impacting drug release from the coating or from the particles.

Figure 1:
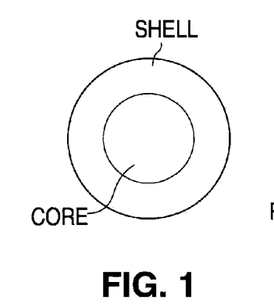
FIG. 1 is a depiction of a nanoshell.

Nanoshells are particles with a core and a shell or a core and two or more layers. FIG. 1 depicts an exemplary nanoshell which has a core and a shell where the thickness of the shell is exaggerated. The shell is a conducting material such as a metal, and the core is preferably non-conducting. However, it is only required that at least one layer has a lower dielectric constant than the adjacent inner layer or the adjacent core.

These nanoshells of this invention undergo a phenomenon known as plasmon resonance which is the collective coupling of the electrons in the metal of the shell with the incident electromagnetic radiation. The plasmon resonance can be dominated by absorption or scattering of the electromagnetic radiation. The wavelength at which the maximum plasmon resonance occurs can be "tuned" by altering the ratio of the shell thickness to the core thickness, or the ratio of the layer thicknesses. In general, for a given core radius, the wavelength at which maximum resonance occurs becomes longer as the shell becomes thinner. The ratio of shell thickness to core radius may vary from 10 to $10^{-3}$. The wavelength at which plasmon resonance occurs may range from 400 nm to 20 µm. A non-limiting example of an operable nanoshell for the purposes of this invention is one with a core diameter in the range of about 55 and about 210 nm with a gold shell in the range of about 5 and about 25 nm (see, e.g., Oldenburg S. J., et al., *Applied Physics Letters;* Vol. 75(19):2897-2899 (1999); Oldenburg S. J., et al., *Chemical Physics Letters* 288:243-247 (1998)).

The core may be composed of dielectric materials or semiconductor materials. Exemplary but non-limiting core materials include colloidal silica, silicon dioxide, titanium dioxide, polymethyl methacrylate (PMMA), polystyrene, and gold sulfide, and semiconductor materials such as, without limitation, CdSe, CdS, or GaAs. The shell material is preferably a conducting material, such as a metal, e.g. without limitation, the noble metals and coinage metals, or an organic conducting material such as polyacetylene and doped polyanaline. More specifically the shell may include, but is not necessarily limited to, metals such as gold, silver, copper, platinum, palladium, lead, iron, biodegradable metals such as magnesium, zinc, calcium, or tungsten, and alloys and combinations thereof.

For use in the present invention, nanoshells with plasmon resonance wavelengths in the range of 900 nm to 1200 nm or in the near-infrared from 650 nm and 900 nm are preferred. The near-infrared spectrum between 650 nm and 900 nm in particular readily permeates living tissue.

The nanoshells may be 5-500 nm in diameter, preferably about 10 to about 300 nm, and more preferably about 15 to about 200 nm. The outer shell layer of the nanoshells may have a thickness in the range between about 1 nm and about 100 nm. The nanoshells can be any shape such as, without limitation, spherical, rod or fiber shaped. However, a spherical or nearly spherical shape is preferred. It is preferable that the nanoshells have a relatively low polydispersity. In some embodiments, the D90/D10 of the nanoshells is not more than 5, not more than 4, not more than 3, or not more than 2.

In a preferred embodiment, the shell is silver or gold and the core is silica.

More details on the nanoshells are described in U.S. Pat. No. 6,685,986, incorporated by reference herein, which includes a method of manufacturing nanoshells in Examples I-V. Other relevant patents and patent application publications include U.S. Pat. Nos. 6,660,381, 6,699,724, and U.S. Patent application publications 2002/0061363, 2002/0132045, 2002/0187347, 2002/0164064, and 2005/0056118, all of which are incorporated by reference herein.

In other embodiments, a different form of nanoshells is used. This form of nanoshell has a core or shell of iron, iron oxide or other materials that heat up when exposed to a fluctuating magnetic field. In addition to iron and iron oxide, lanthanides such as samarium, gadolinium, europium and terbium, elements such as tantalum and molybdenum, and combinations, mixtures, and alloys thereof, may be used.

Figure 2A:
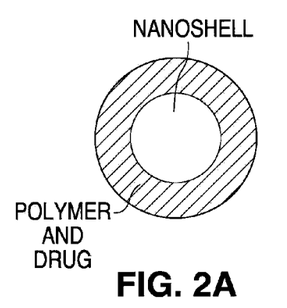
FIG. 2 depicts an exemplary embodiment of particles of the present invention.
Figure 2B:
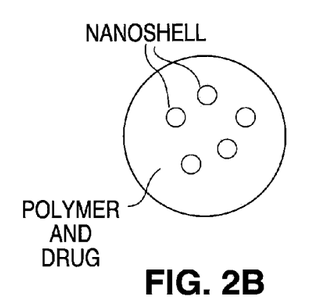
Figure 3A:
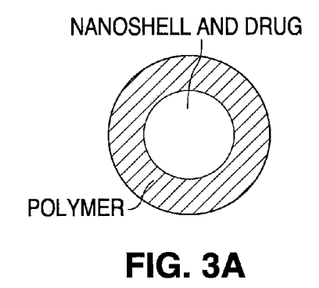
FIG. 3 depicts a second exemplary embodiment of particles of the present invention.
Figure 3B:
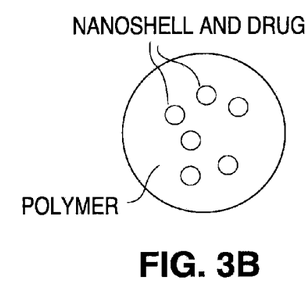
Figure 4A:
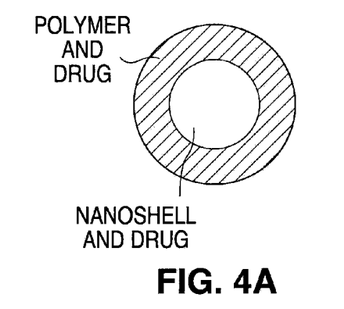
FIG. 4 depicts a third exemplary embodiment of particles of the present invention.
Figure 4B:
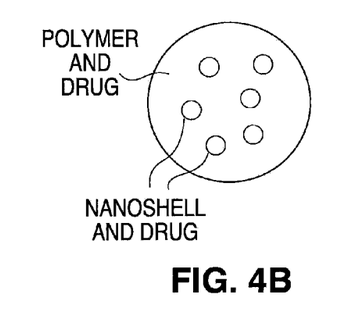
Figure 5A:
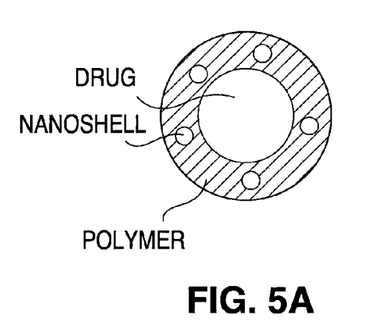
FIG. 5 depicts a fourth exemplary embodiment of particles of the present invention.

Compositions of the present invention include particles and coatings containing nanoshells. The particles are microparticles or nanoparticles comprising a polymer. Non-limiting exemplary embodiments of particles are illustrated in FIGS. 2-5. In the embodiments illustrated in FIGS. 2A, 3A, and 4A, a polymer matrix surrounds a nanoshell. In the embodiments illustrated in FIGS. 2B, 3B, and 4B, one or more nanoshells are embedded in a polymer matrix. In FIGS. 2A and 2B, the polymer matrix includes the drug, and in FIGS. 3A and 3B, the drug is associated with the nanoshells. FIGS. 4A and 4B illustrate embodiments that combine both features as drug is in the polymer matrix and associated with the nanoshells. FIG. 5A depicts an embodiment in which the drug forms a central core which is surrounded by a shell of a polymer matrix including nanoshells. Although the nanoshells illustrated in FIGS. 2B, 3B, 4B, and 5A are shown as encapsulated in the polymer matrix, some of the nanoshells may not be entirely surrounded by the polymer matrix and may be present at the surface. Similarly, for a coating on an implantable medical device including nanoshells, the nanoshells may be dispersed or embedded in the coating, and some of the nanoshells may not be entirely surrounded by polymer. Alternatively, an additional coating layer may be disposed over the layer including the nanoshells such that all nanoshells would be entirely or substantially surrounded by polymer.

For polymer matrices, such as those illustrated in FIGS. 2A, 2B, 4A, and 4B, and a coating on a device, the polymer matrix may be a solid solution in which the drug is dissolved, or essentially dissolved, or the drug and polymer may form separate phases, or a combination thereof. The polymer forms a continuous phase in the polymer matrix, and the drug, if present as a separate phase, may form a co-continuous phase, or may form discrete domains that do not connect to form a continuous network. Preferably, the drug does not form a continuous phase. The drug may be distributed uniformly or non-uniformly throughout the polymer matrix. The ratio of polymer to drug, on a mass basis, may vary from about 1:1 to about 10:1, preferably from about 2:1 to about 8:1.

Figure 5B:
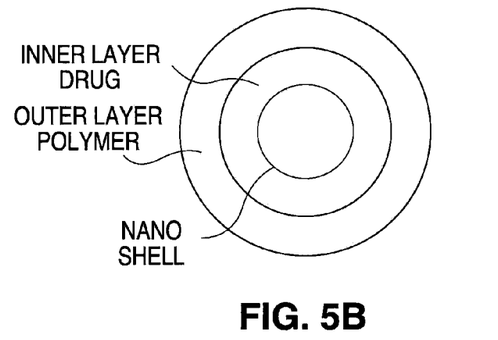

Another non-limiting exemplary embodiment is shown in FIG. 5B which depicts a nanoshell at the core, with a drug-rich inner shell, and an outer shell of a polymer matrix which functions as a rate-limiting membrane or layer. Similarly, a coating on a device may have one drug-rich layer which may be referred to as a drug reservoir layer, and a subsequent layer including the nanoshells disposed over the drug reservoir layer, which may be referred to as a rate limiting layer. The polymer forms a continuous phase in the rate limiting layer whether part of a coating or a particle (such as illustrated in FIG. 5B). It is not required that the polymer form a continuous matrix in the inner shell of the embodiments of FIG. 5B, or in the drug reservoir layer of a coating on a device, but the polymer or other material of the layer binds the layer together and keeps it sufficiently attached to the layer or substrate below. The mass percent drug in the inner layer or drug reservoir layer may vary from about 5% to about 100%, that is, in some embodiments, the inner layer or drug reservoir layer may be essentially completely drug.

In some embodiments, a drug which may be the same as or different from the drug of the inner layer or drug reservoir layer, may be added to the outer layer or rate controlling layer.

If a drug is associated with the nanoshells, such as the embodiments of FIGS. 3A, 3B, 4A, and 4B, the drug may be included in an outer coating around the nanoshells. Alternatively, the nanoshells may have a core including the drug with two outer shells, one outer shell having a lower dielectric constant than the adjacent inner layer. In another alternative embodiment, the core may include drug and a higher dielectric constant material. For nanoshells with drug in the core, the outer layer would need to be made from a material through which the drug can diffuse, or made with pores, such as a porous metal. A non-limiting example is a particle having a first shell, closest to the drug containing core, which is a polymer that has semiconducting properties, or a polymer with embedded material such as silica resulting in a dielectric constant higher than that of the outer layer. The outer layer of the particle may be a partial shell or a porous shell of metal, or a shell of a conducting polymer through which the drug is able to diffuse. Coatings for implantable medical devices may include nanoshells with drug associated with the nanoshells as described above.

Coatings for implantable medical devices may comprise drug in any type of formulation, such as particles, liposomes, etc., where the particle, liposomes, etc. is free of nanoshells. Thus, in some embodiments, a coating may comprise particles with a polymer, and nanoshells in the coating separate from the drug-containing particles. Embodiments encompass inclusion of the polymer having a transition in the above range in the drug containing particles, in the coating, and both in the particles and the coating.

The particles of the present invention may be from about 20 nm to several micrometers in diameter. Preferably, the particles are 50 nm to 10 µm, and more preferably from 50 nm to 500 nm, and even more preferably, from 50 nm to 250 nm in diameter.

The particles or coatings of the present invention include at least one polymer. The polymer, or a segment thereof if it is a block copolymer, has a glass transition temperature, $T_g$, or a crystalline melting temperature, $T_m$ that, when plasticized under physiological conditions, is in the range of 40-60° C., preferably 40-50° C., and more preferably 40-45° C. In some embodiments, the $T_g$ is that of a blend of polymers, or of a polymer plasticized with a plasticizer, which may also be a drug. These temperatures are close to body temperature, and thus heating to above the $T_g$ or $T_m$ will not result in injury to tissue. As used herein, "plasticized under physiological conditions" will refer to plasticization with water at a pH of about 6.5 to 7.5 and a temperature of about 37° C.

In order to obtain triggered drug release, the polymer that is affected by heat from the nanoshells either controls, or is a significant factor in controlling, drug release from the particles or the coating. Thus, if heating by the nanoshells results in raising the temperature of the polymer above its $T_g$ or its $T_m$, the drug release will change if the polymer volume fraction in the polymer matrix is at or above the percolation threshold, or forms a continuous phase. As an example where a significant change in drug release would not be expected is if the segment of a block copolymer that has a $T_g$ or $T_m$ in the temperature ranges above forms discrete and discontinuous regions within a matrix of the other segment which is not impacted by the heating of the nanoshells. In such case, the drug diffusivity through the matrix may not be significantly impacted by the heating from the nanoshells as the continuous phase or matrix is unaffected by the heating.

In general, optimal performance is obtained if the volume fraction of the polymer, or segment or portion of the polymer that undergoes transition due to heating by the nanoshells is at or above the percolation threshold so that a continuous phase is formed. Upon heating, diffusivity changes as a result of the polymer, segments of a polymer, or portions of the polymer melting or changing to a rubbery state, and drug release may be increased if the diffusivity change occurs for a continuous phase. Thus, the volume fraction of crystalline regions in a semi-crystalline polymer with a $T_m$ in one of the above ranges is preferably at or above the percolation limit. For a semi-crystalline polymer, the percolation threshold may be higher for small crystals. The crystallinity of the semi-crystalline polymer may be at least 25%. In some embodiments, the crystallinity may be at least 35%, at least 50%, or at least 70%.

Likewise, the polymer, portion of a polymer blend, or segment of a block copolymer, with a $T_g$ in one of the above ranges is preferably at or above the percolation limit. For a block copolymer, the segment lengths may be long enough to form separate phases. In some embodiments, it is a sum of volume fractions of crystalline regions with a $T_m$ as above and amorphous polymer or regions with a $T_g$ as above that may be at or above the percolation limit.

In some embodiments, the volume fraction of polymer, or portions of the polymer with a $T_g$ or $T_m$ in one of the above ranges may be about 30% or greater, preferably about 40% or greater, and more preferably about 50% or greater of the polymer matrix.

In preferred embodiments, the volume fraction of the drug, if present as a discrete phase is present at a volume fraction below its percolation threshold. In preferred embodiments, if drug is present as a drug-rich phase, as opposed to being dissolved in or homogeneously blended with the polymer, the drug-rich phase is present at a volume fraction below its percolation threshold. In some embodiments, the drug rich phase is at least 30% by volume drug, preferably at least 40% by volume drug, and more preferably, at least 50% by volume drug. There may be multiple drug-rich phases.

If the amorphous regions of a semi-crystalline polymer in a blend have a $T_g$ below 40° C., it is preferred that it is not present as a continuous phase. In other words, it is preferred that the sum of the volume fractions of such regions is below the percolation threshold. However, this is not required. Similarly, it is preferred, but not required, that the sum of the volume fraction of drug and any other soluble substances, which may include another drug, is lower than the percolation threshold.

Biocompatible polymers may be used in manufacturing the particles or coatings. The polymer may be biodegradable or biostable. Blend of polymers, including blends of biodegradable or biostable polymers, may be used. Poly(N-isopropylacrylamide) and copolymers thereof with acrylamide are excluded.

Preferred polymers for the compositions of the present invention are biodegradable polymers and biostable polymers such as poly(ethylene glycol) or copolymers comprising segments of poly(ethylene glycol). Presently preferred polymers include, without limitation, poly(L-lactide-co-glycolide), poly(D,L-lactide), poly(L-lactide), polyglycolide, poly(D,L-lactide-co-glycolide), poly(glycolide), polycaprolactone, poly(lactide-co-caprolactone), poly(glycolide-co-caprolactone), biodegradable polyurethanes, poly(hydroxybutyrate), poly(hydroxyvalerate), poly(ethylene glycol), poly(ethylene glycol)-poly(L-lactide) diblock copolymers, poly(ethylene glycol)-poly(L-lactide-glycolide) diblock copolymers, poly (L-lactide-glycolide)-poly(ethylene glycol)-poly(L-lactide-glycolide) triblock copolymers, poly(hydroxybutyrate-co-valerate), block copolymers of poly(ethylene oxide) and poly (propylene oxide), polyphosphoester urethane, poly(amino acids), poly(trimethylene carbonate), co-poly(ether-esters), polyphosphazenes, and combinations thereof.

The compositions of the present invention are useful for drug delivery. The nanoshells may be "activated" to modulate drug release. As used herein, the term "activated," when used with respect to nanoshells, means that the nanoshells, or particles or coatings including nanoshells, are exposed to electromagnetic radiation of the proper wavelength, or a fluctuating magnetic field or microwave field, depending upon the type of nanoshells, resulting in heating of the nanoshells. The hot nanoshells heat the polymer of the composition and as a result the temperature of the polymer exceeds its operative transition temperature ($T_g$ or $T_m$), that is, the one that is in the temperature ranges mentioned above. Drug diffusion rates in polymers are higher above the glass transition temperature of the polymer or in the polymer melt, and thus the drug release rate increases. A burst release of the drug may be triggered by activating the nanoshells.

The release of drug from the polymer particles or coatings of the present invention does not occur all at once upon activation of nanoshells. Therefore, the increased release may be triggered multiple times, and a pulsatile release profile may be obtained. After the nanoshells are activated, the release may gradually increase to a peak and then slowly decrease. The increase in the release rate is not necessarily the same each time the nanoshells are activated, and drug depletion will lead to a decrease in the peak release rate after activation as the number of times the nanoshells are activated increases.

It is understood that some drug may diffuse from a coating or particles of this invention even when the nanoshells have not been activated, and this release will be referred to as the "background release rate" or the "background release profile." The background release rate is impacted by the amount and the distribution of drug in the particle or coating, and the extent of water diffusion into the polymer. Activation of the nanoshells, however, will substantially increase the rate of diffusion over this background rate. Embodiments of the present invention encompass a peak release rate, after the activation of the nanoshells, which is at least 10%, at least 20%, or at least 40% greater than the background release rate.

A coating of this invention will contain a plurality of nanoshells sufficient to be able to heat the polymer of the coating to a temperature above its $T_g$ or $T_m$. If drug-containing particles are used and the particles include nanoshells, it is the intent of this invention that each particle include at least one nanoshell. Due, however, to the vagaries of fabrication, some particles may not contain nanoshell(s). A composition in which substantially all the particles contain nanoshells is within the scope of this invention. In some embodiments, a plurality of particles of this invention will contain a sufficient number of nanoshells to heat the polymer of substantially all the particles to a temperature above its $T_g$ or Tm. In fact, in some embodiments, the plurality of particles intentionally includes some particles devoid of nanoshells to provide the desired overall drug release profile.

Nanoshells that are activated at different wavelengths or by different mechanisms may be included in the plurality of particles, either within individual particles, and/or in different individual particles of the plurality. The plurality may be a blend of particles of different types. The types of particles may differ in the nanoshells included within the particles, the polymer and/or drug used, the structure of the particle, such as the various illustrated in FIGS. 2-5, or the like. Likewise, nanoshells activated at different wavelengths or by different mechanisms may be included in a coating.

In some embodiments, the particles include more than one drug. Thus, embodiments encompass particles or coatings for which release of two or more drugs is modulated. Specific non-limiting embodiments include particles whether nanoparticles or microparticles, and coatings for the dual drug release of both a statin drug and an anti-inflammatory drug, or dual drug release of a statin drug and fenofibrate. The release of both (or more than one) drug is activated or triggered by exposure to electromagnetic radiation of the proper wavelength, and/or a fluctuating magnetic field or microwave field, depending upon the type(s) of nanoshells.

The compositions of this invention may also include other components such as, but not limited to, wetting agents, lubricating agents, fillers, plasticizing agents, surfactants, diluents, mold release agents, agents which act as drug carriers or binders, anti-tack agents, anti-foaming agents, viscosity modifiers, anti-oxidants, adhesion promoters, coupling agents, residual levels of solvents, and any other agent which aids in, or is desirable in, the processing of the material, or is useful or desirable as a component of the final product.

A particularly useful additive is a radioopaque contrast agent which would allow the particles or the coating to be visualized in vivo. Examples include barium and calcium. With respect to the particles of the present invention, the core of the nanoshells may include, at least in part, a radioopaque material such as barium sulfate.

Polymeric particles of this invention may be classified as a "matrix type" or "monolithic type," wherein the drug and polymer are substantially homogeneously mixed or "reservoir type," or "microencapsulated type" wherein the drug is contained in a core surrounded by a rate-controlling membrane.

There are various methods that are well known in the art by which the matrix type particles or reservoir particles can be manufactured. Such methods include emulsion solvent evaporation methods, phase separation methods, interfacial methods, extrusion methods, molding methods, injection molding methods, heat press methods, coating or layering processes, spray drying, electrospraying, membrane emulsion, precision particle fabrication and so forth. Specific examples of manufacturing processes for matrix type particles may be found in the following U.S. Pat. Nos. 4,954,298; 6,528,093; 4,897,268; 4,293,539; 6,224,794; 7,060,299; and 7,048,947, each of which is incorporated by reference herein. Specific examples for the manufacture of reservoir-type particles may be found in the following U.S. Pat. Nos. 6,767,637 and 4,622,244, each if which is incorporated by reference herein. None of the preceding exemplary art is intended, nor should it be construed, to limit the present invention.

One method that is particularly suitable for the preparation of particles of this invention is emulsion solvent evaporation. The first step in such a method is dissolving the polymer in an organic solvent that is immiscible in water. Typical concentrations for solutions are about 5 w/w % up to about 10 w/w %, while typical concentrations for dispersions are up to about 5 w/w %. Solvents include, but are not limited to, methylene chloride, dichloromethane, chloroform, or ethyl acetate. Next, an emulsion of the organic solvent phase in an aqueous phase is created by ultrasonication. Typical organic solvent to aqueous solvent ratios used are about 1:2 to about 1:20, and the aqueous phase contains emulsifying agents. Non-limiting emulsifying agents include polyvinyl alcohol, polyvinyl pyrrolidone, sodium lauryl sulfate, sodium cholate, TWEEN 80™ (sorbitan monooleate polyethenoxy ether), diacetyl tartaric acid ester of mono-and di-glycerides, glycerol monostearate, glycerol monooleate, glycerol behenate, lecitihin, monosodium phosphate derivatives of mono and di-glycerides, phosphatidyl-choline, stearylamine, and eoxycholic acid.

Subsequently, evaporation of the organic solvent is carried out at atmospheric or under vacuum with continuous stirring of the emulsion. The resulting particles are suspended in the aqueous solution. For the incorporation of hydrophobic drugs, the drug is dissolved in the organic phase which also includes the polymer. As result, the particles suspended in the aqueous solution at the end of the process have the drug encapsulated within.

The emulsion solvent evaporation method is slightly different when the encapsulation of a hydrophilic drug in the particle is desired. Prior to the formation of an emulsion, the hydrophilic drug is dissolved in an aqueous solution including an emulsifying agent as described above. The aqueous solution is then emulsified in the organic phase including the polymer (the first step above) at a ratio of aqueous to organic phase in the initial emulsion of about 1:2 to about 1:20. Here, in contrast to the first situation, the organic phase is the continuous phase and the aqueous drug-containing phase is the discrete phase. Then the same steps are followed as outlined above resulting in the formation of a double emulsion. An aqueous phase is emulsified in an organic phase which in turn is emulsified in a second aqueous phase. In the second emulsion, a typical ratio of the "organic phase" (actually the first emulsion) to the aqueous phase is about 1:100 to about 1:500. Subsequently, the evaporation occurs with continuous stirring as with the first situation.

For both emulsion solvent evaporation methods, more vigorous stirring during the solvent evaporation phase generally leads to smaller particle sizes. The solvent evaporation operation as well as other operations may be performed at lower temperatures if necessary to avoid degradation of a drug and/or denaturing of a protein or peptide. The final step of removing the solvent may be accomplished by supercritical fluid solvent extraction instead of evaporation.

Another method that is particularly suitable for the preparation of particles is precipitation. This method involves dissolving the polymer and drug in an organic phase which is miscible in water. The solution is added to an aqueous solution containing a colloid stabilizer, a non-solvent for the polymer and the drug, such that the polymer and drug precipitate to form particles. The organic solvent is removed from the particles by either evaporation or dialysis.

Spray drying may be used for form particles. Equipment to accomplish spray drying is well known in the art. The polymer and the drug, and optionally a surfactant to reduce particle aggregation, are dissolved or dispersed in a solvent, preferably one with a high volatility. Pressurized air or another gas is also used to atomize the solution or dispersion that is sprayed into a heated chamber to quickly remove the solvent and precipitate the particles. The particle size and other characteristics can be optimized by adjusting the nozzle orifice size and/or type of nozzle used, the flow rate of the solution, the air pressure for the atomization, and the temperature at the spray nozzle, as well as the temperature in the chamber. Solution viscosity may be limiting so the polymer molecular weight is typically about 50 kDa or less, but this is not required.

A particularly useful variation of the spray drying technique involves laminar jet technology which can be combined with electrostatic field, vibrating nozzle, and coaxial fluid (gas or non-solvent) technology. A typical but not-limiting intensity of the electrostatic field is 2-20 kV between the nozzle and a substrate below. A vibrating nozzle allows a laminar jet of fluid to be broken into droplets. Enhancing the electrostatic dispersion of solutions allows for the production of small, highly charged droplets which results in spherical particles. A typical nozzle vibration for a vibrating nozzle is 60 to 120 kHz.

Co-axial fluid technology involves two immiscible fluids. A central fluid contains a drug and it is surrounded by an outer fluid flowing through a concentric annulus. The flow of fluid is broken up to form particles. An annular stream of a second fluid moving at a high velocity can help to make particles smaller than the nozzle opening size (Berkland et al., "Fabrication of PLG Mircrospheres with Precisely Controlled and Monodisperse Size Distributions," *Journal of Controlled Release*, 73: 59-74 (2001)).

A variation of the co-axial fluid technology is precision particle fabrication (Berkland et al., "Precision Polymer Microparticles for Controlled Drug Delivery," *American Chemical Society Symposium* 897: *Carrier Based Drug Delivery*, Chapter 14, pages 197-213, American Chemical Society, 2004). A solution or dispersion of polymer and drug is sprayed through a small nozzle to form a stable laminar jet. In addition to the use of the annular fluid, acoustic energy provided by a piezoelectric transducer which is driven by a wave generator, disrupts the jet thus breaking it into droplets. The ratio of the volume average diameter to the number average diameter for particles manufactured with this method ranged from 1.002 to 1.015.

The methods of forming particles described above may be modified to include nanoshells. The nanoshells may be dispersed in the organic solvent of the emulsion solvent evaporation methods, spray drying, precipitation or other methods. Such methods are more amenable for the production of the embodiments in FIGS. 2B, 3B, and 4B, but precipitation and spray drying methods may result in precipitation of polymer and drug around a single nanoshell. For the embodiments with a single nanoshell in the center, such as FIGS. 2A, 3A, and 4A, particle coating techniques may be used such as, without limitation, a fluid bed with a Wurster insert. Other coating methods known in the art may also be used.

For coatings on devices, the coating may be disposed over the surface of an implantable medical device by any number of methods including, but not limited to, electrostatic coating, plasma deposition, dipping, brushing, or spraying. In a presently preferred embodiment a coating solution is sprayed onto the device. The solution may include the drug and polymer, either dissolved and/or dispersed in a solvent, preferably an organic solvent. The nanoshells may be dispersed in the solution. The spraying may be carried out by atomizing the solution and spraying it onto the device surface while rotating and translating the device underneath the spray nozzles following by rotation and translation under a flow of gas, such as air or nitrogen that may be above room temperature that is above 20° C. to 25° C. Multiple passes underneath the spray nozzles and the gas may be required to obtain a desired layer thickness. Subsequently, the device may be heated to remove residual solvent. Generally a coating layer is the result of the application of the multiple passes in one process before the device is subjected to an operation for the removal of residual solvent, or before a different coating formulation is disposed over the substrate. However, one coating layer may vary in concentration of a substance, such as for example, the drug, if the coating solution does not have the same ratio of drug to other substances in all the passes. With respect to coating layer thickness, it may be in the range of about 0.5 and about 10 μm, or about 0.5 and about 7 μm, or as presently preferred, about 2 and about 7 μm.

The compositions of the present invention can be used for systemic or local drug delivery.

Systemic delivery involves the administration of a drug at a discrete location followed by the dispersal of the drug throughout the patient's body including, of course, to the target treatment site or organ. In order to achieve a therapeutically effective amount of the drug at the target site, it is usually necessary to administer an initial dose substantially greater than the therapeutically effective amount to account for the dilution the drug undergoes as it travels through the body. Systemic delivery is carried out primarily in two ways: introduction of the drug into the digestive tract (enteral administration) or into the vascular system (parenteral administration), either directly such as injection into a vein or an artery or indirectly such as injection into a muscle or into the bone marrow. For the particles of the present invention, enteral administration is not likely to be used, but embodiments of the present invention encompass other forms of systemic administration.

Local delivery comprises administration of the drug directly to the target site. The initial dose can be at or very close to the therapeutically effective amount. With time, some of the locally delivered drug may diffuse over a wider region but such is not the intent of localized delivery and the concentration of the diffused drug will ordinarily be sub-therapeutic, i.e., too low to have a therapeutic effect.

There are a number of techniques for local drug delivery. Local delivery includes local needle injection that is injection by a needle at the site. A drug delivery catheter may be used, that is a catheter designed to deliver fluids to a vein or artery. The fluid may include a plurality of particles of the present invention.

Figure 6:
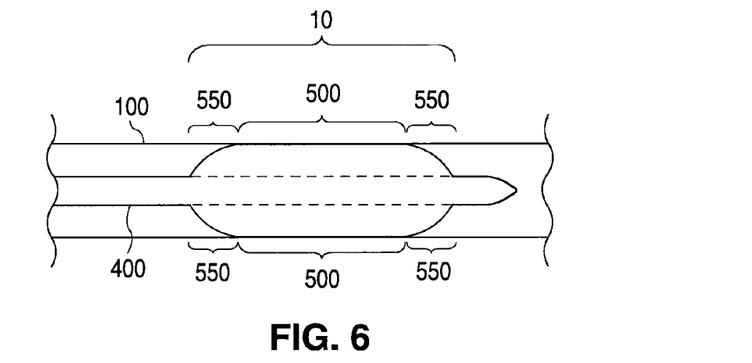
FIG. 6 is a depiction of an expanded balloon at the end of a catheter.
Figure 7:
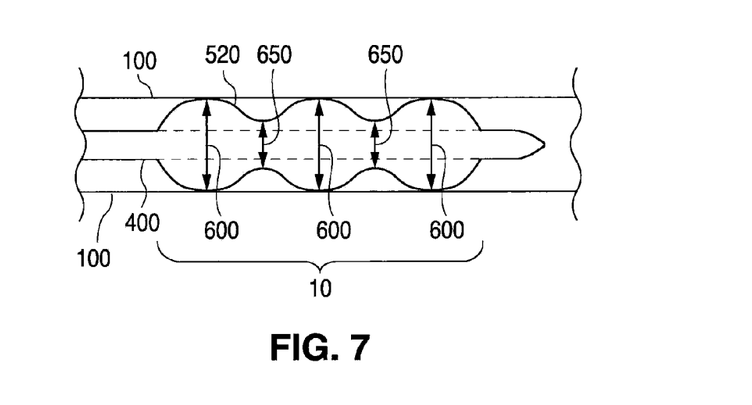
FIG. 7 is a depiction of an expanded multi-balloon at the end of a catheter.

The plurality of particles may be delivered by a coated balloon. Examples of two types of catheter balloons are shown in FIGS. 6 and 7. In FIG. 6, the balloon has substantially a single diameter over its entire length such that the full length of the balloon is in contact with the luminal surface of the vessel. "Substantially" a single diameter is illustrated in FIG. 6, where the ends 550 of balloon 520 are not necessarily square so that the balloon does have a large number of diminishing diameters at the ends as it curves down to join the catheter tube but the major portion of balloon length 500 has substantially the same diameter.

Dual balloons or multiple balloons may also be used as well as a balloon having two different outside diameters, as illustrated in FIG. 7. As shown in FIG. 7, at each end of the balloon is a first diameter, and also potentially at any number of multiple point between the ends. The first diameter is the diameter sufficient to place the balloon in contact with the vessel wall. Each section of the first diameter is separated from each other section of such diameter by a second diameter, which is less than the inside diameter of the vessel and therefore does not contact the vessel surface. Of course, use of the term "a second diameter" is nominal; the point is that there are regions between the first diameters that are not in contact with the vessel surface and the diameters of those regions may be identical or all may be different. FIG. 7 illustrates wherein balloon 620 connected to catheter 400 has first diameters 600, which contact vessel wall 100 and second diameters 650. In other embodiments, there are multiple balloons, similar to the single balloon illustrated in FIG. 6, arranged in a series along the catheter.

The particles may be coated on the exterior of a balloon by either suspension coating that was discussed above, followed by either lyophilization or exposure to a temperature above room temperature to remove solvent. The particles may be dust-coated on the balloon. For balloons with multiple sections contacting the vessel wall, the particles may coat only those sections that are in contact with the vessel surface, only those sections not in contact with the vessel surface, or both. The ends of the balloon may be coated or left uncoated in either of the above embodiments.

The particles of the present invention may be delivered by a microporous balloon, which is a balloon made from a material with small holes, or pores, formed in the material of the balloon. The fluid used to inflate the balloon includes the particles which can flow through the pores. The flow of the fluid including the particles through the pores may be enhanced by increasing the fluid pressure. Similar to the coated balloon, if the balloon has multiple sections in contact with the vessel wall, only those sections in contact with the vessel wall may have pores, or alternatively only the sections between the sections touching the vessel wall may have pores, or both sections may have pores. The ends of the balloon may be porous or devoid of pores in either of the above embodiments.

Figure 8A:
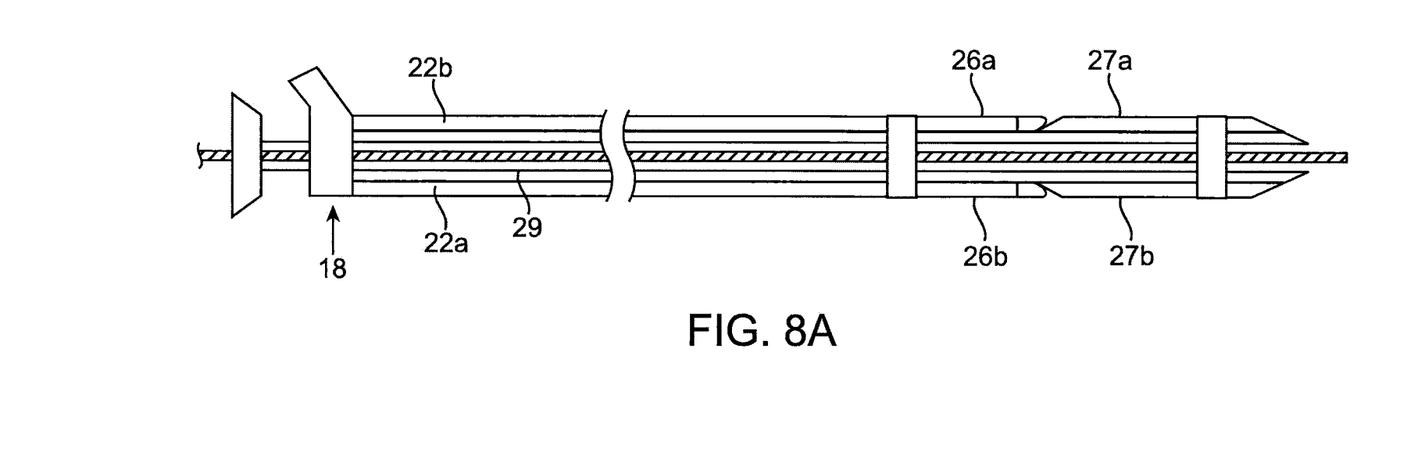
FIGS. 8A and 8B are depictions of an injection catheter.
Figure 8B:
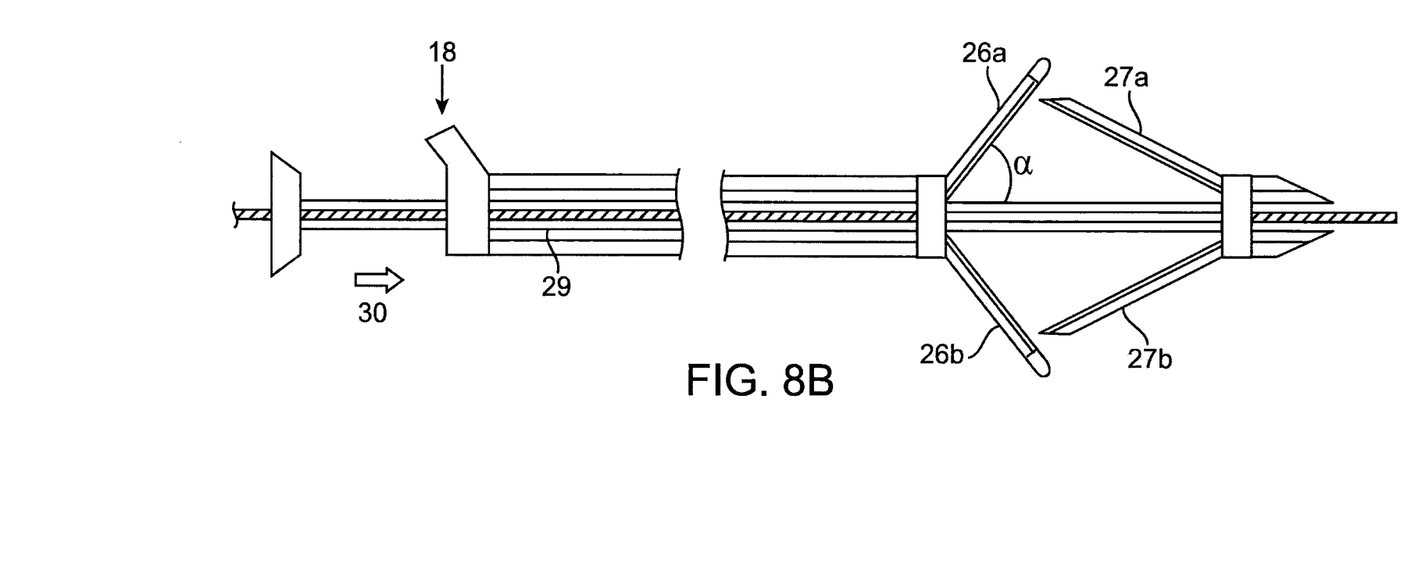

Another manner of delivering the particles of the present invention is a catheter including a needle or syringe for injection into the tissue. FIGS. 8A and 8B depict an exemplary embodiment of a needle injection catheter in the undeployed and deployed states, respectively. The assembly includes a central guidewire tube 29 surrounded by drug delivery lumens 22a and 22b. Drug delivery port 18 allows for delivery of drug substances into delivery lumens 22a and 22b. Needles 26a and 26b and tubes 27a and 27b are aligned parallel with central guidewire tube 29 in FIG. 8A. However, as illustrated in FIG. 8B, after movement of drug delivery port 18 in the direction of arrow 30, hollow needles 26a and 26b are forced out at an angle, $\alpha>0$, and held in this position by tubes 27a and 27b. When needles 26a and 26b are forced out, the needles can penetrate the tissue or the wall of the lumen, thus allowing medication to be injected via injection port 18. After drug delivery is complete, the delivery port 18 is pulled back (in a direction opposite to that shown by arrow 30), thus allowing the hollow needles 26a and 26b to return to their original position.

Figure 9:
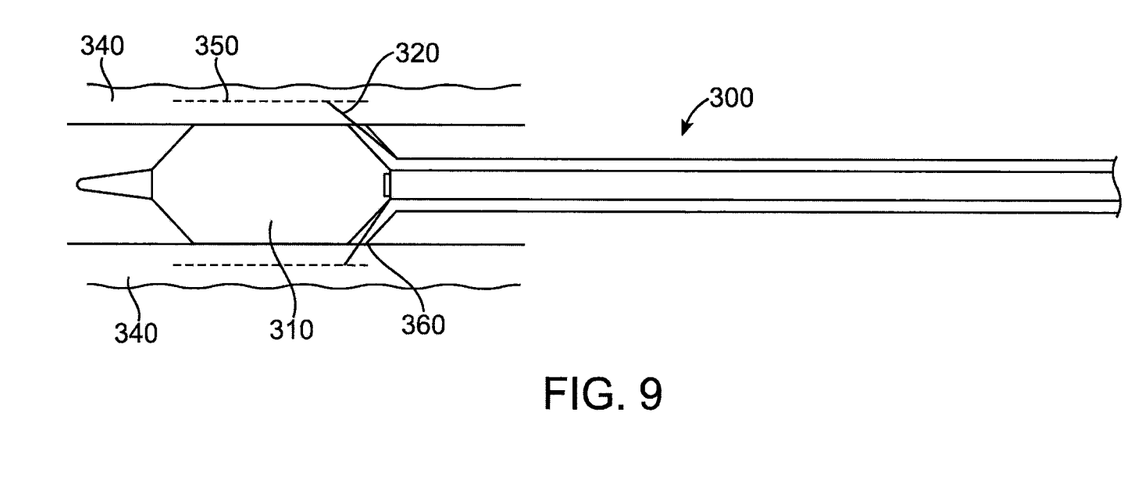
FIG. 9 is a depiction of an exemplary embodiment of an injection balloon and catheter assembly.

Some injection catheters utilize a balloon to deploy the needles. One exemplary embodiment of an injection balloon catheter for cardiovascular applications is that of U.S. Pat. No. 6,692,466. A schematic drawing of the injection balloon catheter is shown in FIG. 9. The catheter 300 has been inserted into a lumen whose walls are represented by 340 in FIG. 9. The balloon 310 disposed on the catheter 300 is depicted in the inflated state. The catheter assembly includes an inflation lumen which is used to inflate the balloon by supplying fluid through the lumen.

As illustrated in FIG. 9, the needle is in fluid communication with a delivery lumen. The end of the delivery lumen includes an exit notch 360. Inflation of the balloon pushes the needle exit notch 360 into the tissue 340. Subsequently, the needle 320, which is in fluid communication with a delivery lumen, can be pushed to puncture, or penetrate, the tissue 340. The device includes a mechanism to control the depth of needle penetration. The needle can be either pre-filled with the drug formulation to be delivered, or can be coupled to dispensing means known in the art, such as but not limited to, a syringe or fluid pump.

Another manner of local delivery of the particles of the present invention is by use of an implantable device such as a stent. The particles including the nanoshells may be included in a coating disposed over the device. Such embodiments differ from disposing over a device surface a coating of polymer, drug, and nanoshells because in the former embodiment, the polymer, drug, and nanoshells are preformed into particles that are subsequently coated onto the device. A metallic stent, a polymeric stent, or a biodegradable stent, whether fabricated from a biodegradable polymer, a bioerodable metal, or a combination thereof, may be coated. Any type of stent may be coated including, without limitation, a balloon expandable stent, or a self-expandable stent. The material of the device is not limited. The particles may be coated onto the stent, or other device, using similar techniques to those described above for coating a balloon. The particles may be incorporated in a biodegradable implantable medical device, such as a stent, or in a biodegradable implant that is implanted into the tissue. If incorporated in a biodegradable device or implant, the particles are released to the local site as the device or implant degrades.

Embodiments including delivery of the particles via a coating on a device, or via a biodegradable implant or device, encompass delivery of the drug by drug diffusion through the coating or device into the patient's body, and/or release of the particles form the device or the coating with subsequent release of the drug from the particles. Thus, the coating or device may be designed to quickly dissolve or erode, thus releasing the particles from the device or coating such that the drug is substantially or primarily released from the particles. In some embodiments, not less than 70%, preferably not less than 80%, of the drug is released after the particles are released from the coating. Alternatively, the composition may be in a coating of a device that does not erode or dissolve with the particles included primarily to allow for modulation of release from the coating. If a coating includes nanoshells, a polymer, and a drug, but these are not all present in particles, the drug release is primarily due to diffusion through the coating.

Coatings of the present invention that include a polymer, a drug, and a plurality of nanoshells, and the particles of the present invention that also include a polymer, a drug, and one or more nanoshells, may be combined. The drug, polymer, and type of nanoshell in the particles may be the same or different from those of the coating. The material of the device is not a limitation.

Other types of catheters, balloons, injection catheters, or devices designed for local injection or administration may be used, as well as other types of implants or implantable devices in addition to those described herein. The embodiments of methods of treatment using the plurality of particles of the present invention are not limited to those exemplary devices described herein.

Once the particles have been administered to a patient (animal, including a human) or the a medical device including nanoshells in a coating and/or the body of the device has been implanted, the nanoshells may be activated by exposure to electromagnetic radiation of the appropriate wavelength, a fluctuating magnetic field, or a microwave field. In preferred embodiments, the exposure is done internally, that is via a catheter or the like, such that exposure is limited to the area of treatment, thus avoiding injury to healthy tissue. As a non-limiting example a light guide such as a fiber optic type wire or cable, may be attached to a catheter to allow it to be maneuvered to the treatment region, or it may form an integrated part of a catheter. The light guide may be capable of providing electromagnetic radiation at the appropriate wavelength, such as, without limitation, the near infrared.

However, extracorporeal activation is also encompassed in the various embodiments of the invention. In particular, magnetic resonance equipment may be used external to the body to activate the nanoshells. Drug delivery from the compositions of the present invention may be modulated by activation externally. The external activation may be triggered or initiated via feedback from a diagnostic device. Such coupling of a diagnostic device to the manner of external activation allows for a self-regulated, externally modulated, on-demand, non-invasive drug delivery system. Thus, some embodiments of the present invention may be a drug delivery system including particles or coatings as described above, a diagnostic device, and a an external manner of activating at least some of the nanoshells of the particles and/or coating. In some embodiments the system includes a diagnostic device coupled to an external activation device.

The compositions of the present invention may be used to treat any number of diseases and conditions depending upon the drug used. Some non-limiting examples include vulnerable plaque, restenosis, peripheral vascular disease, small vessel bifurcations and cancer. In some embodiments, the self-regulated, externally modulated, on-demand, non-invasive drug delivery systems described in the previous paragraph may be used for cardiovascular applications as well as other applications.

Polymers

Other polymers may be used in the coatings and particles in addition to the polymer with the melting temperature or glass transition temperature in one of the above cited ranges. Representative polymers that may be used in the particles and coatings of the present invention, that may or may not have a melting temperature or glass transition temperature in one of the above cited ranges, include, but are not limited to: poly (N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoesters, polyanhydrides, poly(glycolic acid), poly(glycolide), poly(L-lactic acid), poly (L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly (glycolide-co-caprolactone), poly(trimethylene carbonate), poly(ester-amide) polymers generally, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose, ethylene vinyl alcohol copolymer (commonly known by the generic name EVOH or by the trade name EVAL™), poly(butyl methacrylate), poly (vinylidene fluoride-co-hexafluoropropene) (e.g., SOLEF 21508™, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol, and combinations thereof.

Drugs

Examples of drugs that may be suitable for use in the compositions and methods of this invention depending, of course, on the specific disease being treated, include, without limitation, anti-restenosis, pro- or anti-proliferative, anti-inflammatory, anti-neoplastic, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective drugs.

Examples of antiproliferative drugs include, without limitation, actinomycins, taxol, docetaxel, paclitaxel, sirolimus (rapamycin), biolimus A9 (Biosensors International, Singapore), deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin (a structural derivative of rapamycin), 40-O-[2-(2-hydroxy)ethoxy]ethyl-rapamycin (a structural derivative of rapamycin), 40-O-tetrazole-rapamycin (a structural derivative of rapamycin), 40-O-tetrazolylrapamycin, 40-epi-(N1-tetrazole)-rapamycin, and pirfenidone.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopro­fen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexametha­sone acetate, dexmethasone phosphate, momentasone, corti­sone, cortisone acetate, hydrocortisone, prednisone, pred­nisone acetate, betamethasone, betamethasone acetate, diclofenac potassium, diclofenac sodium, diflorasone diac­etate, diflumidone sodium, diflunisal, difluprednate, diftal­one, dimethyl sulfoxide, drocinonide, endrysone, enlimo­mab, enolicam sodium, epirizole, etodolac, etofenamate, felbinac, fenamole, fenbufen, fenclofenac, fenclorac, fen­dosal, fenpipalone, fentiazac, flazalone, fluazacort, flufe­namic acid, flumizole, flunisolide acetate, flunixin, flunixin meglumine, fluocortin butyl, fluorometholone acetate, flu­quazone, flurbiprofen, fluretofen, fluticasone propionate, furaprofen, furobufen, halcinonide, halobetasol propionate, halopredone acetate, ibufenac, ibuprofen, ibuprofen alumi­num, ibuprofen piconol, ilonidap, indomethacin, indometha­cin sodium, indoprofen, indoxole, intrazole, isoflupredone acetate, isoxepac, isoxicam, ketoprofen, lofemizole hydro­chloride, lomoxicam, loteprednol etabonate, meclofenamate sodium, meclofenamic acid, meclorisone dibutyrate, mefe­namic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydro­chloride, pentosan polysulfate sodium, phenbutazone sodium glycerate, pirfenidone, piroxicam, piroxicam cinnamate, piroxicam olamine, pirprofen, prednazate, prifelone, pro­dolic acid, proquazone, proxazole, proxazole citrate, rimex­olone, romazarit, salcolex, salnacedin, salsalate, sangui­narium chloride, seclazone, sermetacin, sudoxicam, sulindac, suprofen, talmetacin, talniflumate, talosalate, tebufelone, tenidap, tenidap sodium, tenoxicam, tesicam, tesimide, tetry­damine, tiopinac, tixocortol pivalate, tolmetin, tolmetin sodium, triclonide, triflumidate, zidometacin, zomepirac sodium, aspirin (acetylsalicylic acid), salicylic acid, corticos­teroids, glucocorticoids, tacrolimus and pimecrolimus.

Examples of antineoplastics and antimitotics include, without limitation, paclitaxel, docetaxel, methotrexate, aza­thioprine, vincristine, vinblastine, fluorouracil, doxorubicin hydrochloride and mitomycin.

Examples of anti-platelet, anticoagulant, antifibrin, and antithrombin drugs include, without limitation, heparin, sodium heparin, low molecular weight heparins, heparinoids, hirudin, argatroban, forskolin, vapiprost, prostacyclin, pros­tacyclin dextran, D-phe-pro-arg-chloromethyl ketone, dipy­ridamole, glycoprotein IIb/IIIa platelet membrane receptor antagonist antibody, recombinant hirudin and thrombin, thrombin inhibitors such as ANGIOMAX® (bivalirudin, from Biogen), calcium channel blockers such as nifedipine, colchicine, fish oil (omega 3-fatty acid), histamine antago­nists, lovastatin, monoclonal antibodies such as those specific for Platelet-Derived Growth Factor (PDGF) receptors, nitro­prusside, phosphodiesterase inhibitors, prostaglandin inhibi­tors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of cytostatic or antiproliferative drugs include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibod­ies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of ACE inhibitors include, without limitation, quinapril, perindopril, ramipril, captopril, benazepril, tran­dolapril, fosinopril, lisinopril, moexipril and enalapril.

Examples of angiogensin II receptor antagonists include, without limitation, irbesartan and losartan.

Examples of statins, a class of drugs that can reduce low density lipoproteins, also referred to as "bad cholesterol," by means of blocking an enzyme in the liver used to manufacture cholesterol. Non-limiting examples of statins are lovastatin, simvastatin, atorvastatin, fluvastatin, pravastatin, and rosuv­astatin.

Anti-inflammatory drugs generally include steroidal and nonsteroidal anti-inflammatory drugs. Examples of steroidal anti-inflammatory drugs include, without limitation, 21-ac­etoxypregnenolone, alclometasone, algestone, amcinonide, beclomethasone, betamethasone, budesonide, chloropred­nisone, clobetasol, clobetasone, clocortolone, cloprednol, corticosterone, cortisone, cortivazol, deflazacort, desonide, desoximetasone, dexamethasone, diflorasone, diflucor­tolone, difluprednate, enoxolone, fluazacort, flucloronide, flumethasone, flunisolide, fluocinolone acetonide, fluocino­nide, fluocortin butyl, fluocortolone, fluorometholone, flu­perolone acetate, fluprednidene acetate, fluprednisolone, flu­randrenolide, fluticasone propionate, formocortal, halcinonide, halobetasol propionate, halometasone, halopre­done acetate, hydrocortamate, hydrocortisone, loteprednol etabonate, mazipredone, medrysone, meprednisone, methyl­prednisolone, mometasone furoate, paramethasone, predni­carbate, prednisolone, prednisolone 25-diethylamino-ac­etate, prednisolone sodium phosphate, prednisone, prednival, prednylidene, rimexolone, tixocortol, triamcinolone, triamci­nolone acetonide, triamcinolone benetonide, triamcinolone hexacetonide, any of their derivatives, and combinations thereof.

Examples of nonsteroidal anti-inflammatory drugs include, without limitation, COX-1 and COX nonspecific inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropi­onic acids such as ibuprofen, naproxen, flurbiprofen, keto­profen, fenoprofen and oxaprozin), and selective COX-2 inhibitors (e.g., diaryl-substituted furanones such as rofe­coxib; diaryl-substituted pyrazoles such as celecoxib; indole acetic acids such as etodolac and sulfonanilides such as nime­sulide), and combinations thereof.

Other therapeutic drugs that may find beneficial use herein include, again without limitation, alpha-interferon, geneti­cally engineered endothelial cells, dexamethasone, antisense molecules which bind to complementary DNA to inhibit tran­scription, and ribozymes, antibodies, receptor ligands such as the nuclear receptor ligands estradiol and the retinoids, thia­zolidinediones (glitazones), enzymes, adhesion peptides, blood clotting factors, inhibitors or clot dissolving drugs such as streptokinase and tissue plasminogen activator, antigens for immunization, hormones and growth factors, oligonucleotides such as antisense oligonucleotides and ribozymes and retroviral vectors for use in gene therapy, antiviral drugs and diuretics.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention.

What is claimed:

1. A composition for controlled release of a drug comprising:
    a plurality of particles comprising:
        a polymer which is either an amorphous or semi-crystalline polymer with a glass transition temperature as plasticized under physiological conditions from about 40° C. to about 60° C., or a semi-crystalline polymer having a degree of crystallinity of at least 25% with a melting temperature, as plasticized under physiological conditions, from about 40° C. to about 60° C.;
        a drug; and
        one or more nanoshells capable of producing heat upon exposure to electromagnetic radiation, a fluctuating magnetic field, or a microwave field; wherein
    substantially all of the individual particles of the plurality include one or more of the nanoshells;
    wherein the particles comprise a polymer matrix comprising the polymer and coating the nanoshell; or the particles are composed of a polymer matrix comprising the polymer and nanoshells; or the particles comprise a polymer matrix comprising the polymer and nanoshells, the polymer matrix surrounding a central core; and
    wherein upon exposure to electromagnetic radiation, or a fluctuating magnetic field, or a microwave field, the nanoshells produce sufficient heat to raise the temperature of the polymer above its glass transition temperature or its melting temperature.

2. The composition of claim 1, wherein the glass transition temperature or the melting temperature of the polymer is from about 40° C. to about 50° C.

3. The composition of claim 1, wherein the average diameter of the particles is about 50 nanometers to about 10 micrometers.

4. The composition of claim 1, wherein the nanoshells comprise gold.

5. The composition of claim 4, wherein the average diameter of the nanoshells is about 15 nanometers to about 200 nanometers.

6. The composition of claim 1, wherein the nanoshells comprise cores comprising a metal selected from the group consisting of iron, iron oxide, lanthanides, samarium, gadolinium, europium, terbium, tantalum, molybdenum, alloys thereof, and combinations thereof.

7. The composition of claim 1, wherein the nanoshells comprise a metal selected from the group consisting of silver, platinum, palladium, chromium, iridium, magnesium, zinc, calcium, tungsten, alloys thereof, and combinations thereof.

8. The composition of claim 1, wherein the polymer is selected from the group consisting of poly(L-lactide-co-glycolide), poly(D,L-lactide), poly(L-lactide), polyglycolide, poly(D,L-lactide-co-glycolide), poly(glycolide), polycaprolactone, poly(lactide-co-caprolactone), poly(glycolide-co-caprolactone), biodegradable polyurethanes, poly(hydroxybutyrate), poly(hydroxyvalerate), poly(ethylene glycol), poly(ethylene glycol)-poly(L-lactide) diblock copolymers, poly(ethylene glycol)-poly(L-lactide-glycolide) diblock copolymers, poly(L-lactide-glycolide)-poly(ethylene glycol)-poly(L-lactide-glycolide) triblock copolymers, poly(hydroxybutyrate-co-valerate), block copolymers of poly(ethylene oxide) and polypropylene oxide), polyphosphoester urethane, poly(amino acids), poly(trimethylene carbonate), poly(ether-esters), polyphosphazenes, and combinations thereof.

9. The composition of claim 1, wherein the drug is selected from the group consisting of actinomycins, taxol, paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus A9, deforolimus, AP23572, temsirolimus, pimecrolimus, 40-O-tetrazolyl-rapamycin, 40-epi-(N1-tetrazole)-rapamycin, pirfenidone, tacrolimus, dexamethasone, rapamycin, 40-O-(2-hydroxy)ethyl-rapamycin(everolimus), 40-O-(3-hydroxy)propyl-rapamycin, 40-O-[2-(2-hydroxy)ethoxy]ethyl-rapamycin, and 40-O-tetrazole-rapamycin, zotarolimus, γ-hiridun, clobetasol, pimecrolimus, imatinib mesylate, midostaurin, and combinations thereof.

10. The composition of claim 1, wherein the composition comprises at least two drugs, the two drugs comprising a statin and an anti-inflammatory drug, or a statin and fenofibrate.

11. The composition of claim 10, wherein the composition is capable of releasing both drugs at an increased release rate after the composition is exposed to electromagnetic radiation, a fluctuating magnetic field, or a microwave field.

12. The composition of claim 1, wherein the particles comprise a polymer matrix comprising the polymer, the polymer matrix coating the nanoshell.

13. The composition of claim 1, wherein the particles comprise a polymer matrix comprising the polymer and nanoshells, the polymer matrix surrounding a central core.

14. The composition of claim 1, whereby the increase in the temperature of the polymer of the particles results in a change in the diffusivity of the drug.

15. The composition of claim 1, whereby the increase in the temperature of the polymer of the particles results in a change in the diffusivity of the drug, and wherein the drug release from the particles is impacted by the change in diffusivity of the drug.

16. A method comprising:
    administering to a patient in need thereof the composition of claim 1; and
    after administration, activating the particles of the composition by exposing the particles to a fluctuating magnetic field, a microwave field, or an electromagnetic radiation to the composition.

17. The method of claim 16, wherein administering the composition comprises systemic or local administration.

18. The method of claim 17, wherein systemic administration comprises intravenous injection, intramuscular injection, or injection into the bone marrow.

19. The method of claim 17, wherein local administration comprises administration selected from the group consisting of administration by a catheter, a coated balloon catheter, a needle-injection catheter, a porous balloon catheter, local needle injection, implantation of a coated stem, implantation of a biodegradable stem, implantation of a biodegradable implant, and combinations thereof.

20. The method of claim 16, wherein the source of the fluctuating magnetic field, the microwave field, or the electromagnetic radiation is outside the patient's body.

21. The method of claim 16, wherein the source of the fluctuating magnetic field, the microwave field, or the electromagnetic radiation is inside the patient's body.

22. The method of claim 21, where the source of the fluctuating magnetic field, the microwave field, or the electromagnetic radiation is in a cathether within the patient's body.

23. The method of claim 16, wherein patient is need of treatment for a disease or condition selected from the group consisting of atherosclerosis, vulnerable plaque, restenosis, peripheral vascular disease, small vessel bifurcations and cancer.

* * * * *